(12) United States Patent
Hawes et al.

(10) Patent No.: US 8,965,599 B2
(45) Date of Patent: Feb. 24, 2015

(54) PASSIVE ENTRY AND PASSIVE START SYSTEM WITH OPERATOR WALKING DETECTION

(71) Applicant: Delphi Technologies, Inc., Troy, MI (US)

(72) Inventors: Kevin J. Hawes, Greentown, IN (US); Todd P. Oman, Greentown, IN (US)

(73) Assignee: Delphi Technologies, Inc., Troy, MI (US)

( * ) Notice: Subject to any disclaimer, the term of this patent is extended or adjusted under 35 U.S.C. 154(b) by 83 days.

(21) Appl. No.: 13/874,513

(22) Filed: May 1, 2013

(65) Prior Publication Data

US 2014/0330448 A1 Nov. 6, 2014

(51) Int. Cl.
*G05F 1/00* (2006.01)
*B60R 25/01* (2013.01)

(52) U.S. Cl.
CPC .................................. *B60R 25/01* (2013.01)
USPC ............... 701/2; 701/8; 701/31.1; 701/32.6; 701/33.9; 340/992; 340/426.16; 340/539.13; 340/539.32; 340/901

(58) Field of Classification Search
CPC .... G01C 17/38; G01C 22/006; G01S 13/825; G01S 5/0205; G06F 15/781; G06F 21/32; G06F 21/44; G06F 2221/2111; H04L 2209/805; H04L 9/3231; H04L 9/3247; H04W 12/06; G07C 2209/63; G07C 9/00309
USPC ...................... 701/2, 32.6, 486, 8, 31.1, 33.9; 340/992, 426.18, 539.13, 901, 902, 340/905
See application file for complete search history.

(56) References Cited

U.S. PATENT DOCUMENTS

| 5,803,230 | A | * | 9/1998 | Canziani et al. ......... 198/370.06 |
| 8,373,581 | B2 | | 2/2013 | Hassan et al. |
| 2004/0183562 | A1 | * | 9/2004 | Hauenstein ................... 324/766 |
| 2009/0198155 | A1 | | 8/2009 | Bonnet |
| 2012/0143094 | A1 | | 6/2012 | Jallon |
| 2012/0256621 | A1 | * | 10/2012 | Fyie et al. ..................... 324/251 |
| 2013/0019292 | A1 | | 1/2013 | Varshavsky et al. |

FOREIGN PATENT DOCUMENTS

| EP | 0 808 971 A2 | 11/1997 |
| EP | 0 984 124 A2 | 3/2000 |
| EP | 1 867 951 A1 | 12/2007 |
| EP | 2 612 795 A1 | 7/2013 |
| FR | 2 926 971 A1 | 8/2009 |
| JP | 2008 039619 A | 2/2008 |
| WO | 2005/124669 A2 | 12/2005 |
| WO | 2010/122174 A1 | 10/2010 |
| WO | 2012/119681 A1 | 9/2012 |

OTHER PUBLICATIONS

European Search Report dated Oct. 2, 2014.

* cited by examiner

*Primary Examiner* — Redhwan K Mawari
(74) *Attorney, Agent, or Firm* — Lawrence D. Hazelton

(57) ABSTRACT

A passive entry passive start (PEPS) vehicle security system configured to activate a vehicle function when an activation signal is received. The system includes a nomadic device configured to detect a change of a magnetic field relative to the nomadic device, and emit an activation signal only if the change corresponds to walking by an operator carrying the nomadic device.

6 Claims, 1 Drawing Sheet

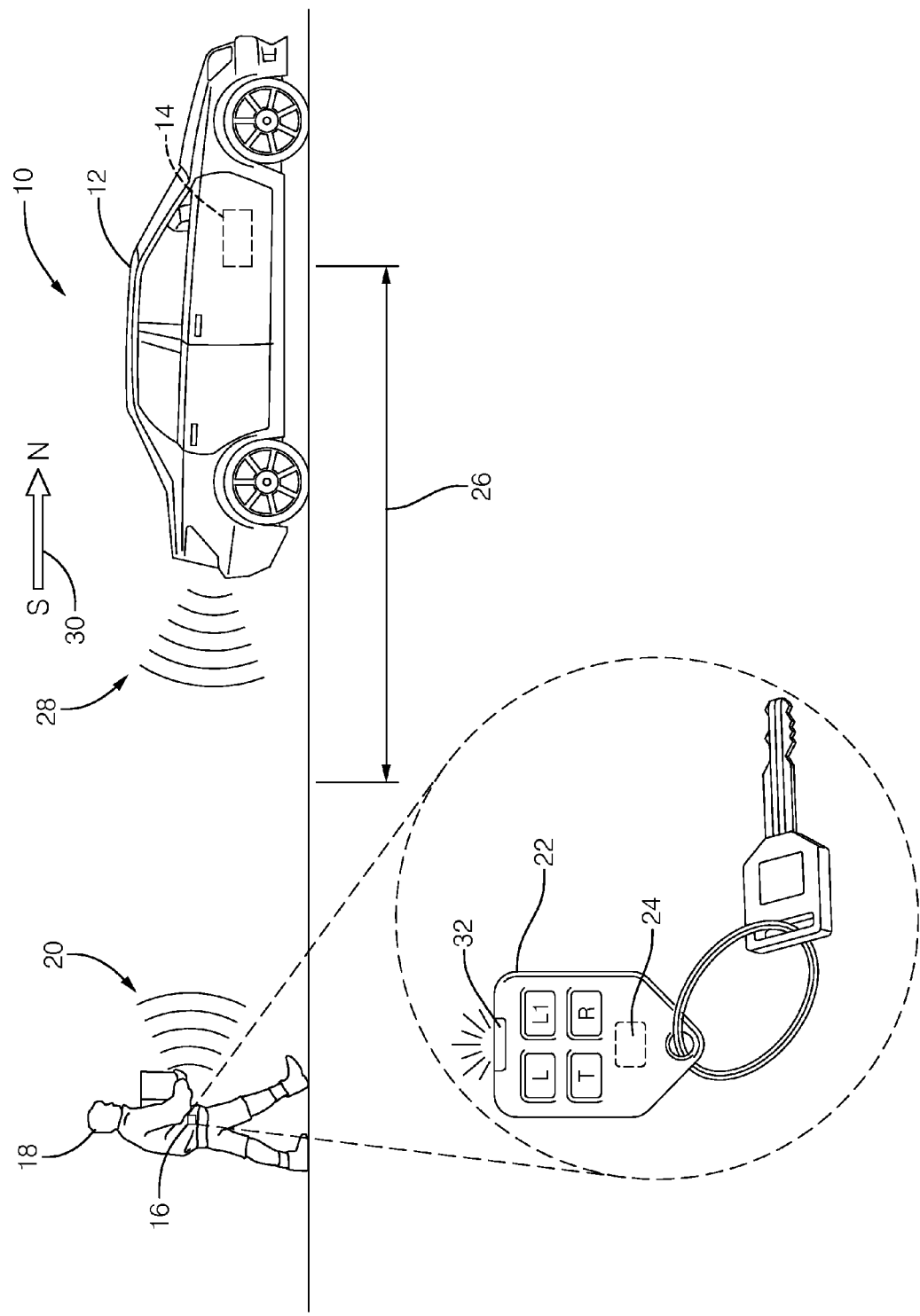

PASSIVE ENTRY AND PASSIVE START SYSTEM WITH OPERATOR WALKING DETECTION

TECHNICAL FIELD OF INVENTION

This disclosure generally relates to passive entry passive start (PEPS) vehicle security system, and more particularly relates to a a nomadic device configured to detect a change of a magnetic field relative to the nomadic device, and emit an activation signal only if the change corresponds to walking by an operator carrying the nomadic device

BACKGROUND OF INVENTION

Passive entry and passive start (PEPS) systems for vehicles have been proposed that rely on a manual wake-up action such as touching or pulling on a door handle to wake-up the system. Such a configuration may lead to a so-called 'wall effect' that caused a brief, but possibly annoying, delay between the manual wake-up action and a vehicle door being unlocked by the PEPS system resulting in the operator attempting to open a locked door. Another configuration has been proposed where the vehicle emits an interrogation signal, or a nomadic device (e.g. a PEPS key fob) emits an activation signal, at regular intervals so the wake-up of the PEPS system is performed as an operator carrying the nomadic device approaches the vehicle. However, this configuration leads to an undesirable energy drain on either the vehicle battery or the nomadic device battery, depending on the PEPS system configuration. What is needed is a relatively long range trigger that initiates nomadic device/vehicle communications without a significant drain on nomadic device or vehicle batteries.

SUMMARY OF THE INVENTION

In accordance with one embodiment, a passive entry passive start (PEPS) vehicle security system is provided. The PEPS system is configured to activate a vehicle function when an activation signal is received. The system includes a nomadic device. The nomadic device is configured to detect a change of a magnetic field relative to the nomadic device, and emit an activation signal only if the change corresponds to walking by an operator carrying the nomadic device.

In another embodiment, a nomadic device is provided. The nomadic device is configured to transmit an activation signal to a vehicle equipped with a passive entry passive start (PEPS) vehicle security system configured to activate a vehicle function when an activation signal is received. The nomadic device includes a magnetic field sensor and a processor. The magnetic field sensor is configured to detect a change of a magnetic field relative to the nomadic device. The processor is configured to emit an activation signal only if the change corresponds to walking by an operator carrying the nomadic device.

Further features and advantages will appear more clearly on a reading of the following detailed description of the preferred embodiment, which is given by way of non-limiting example only and with reference to the accompanying drawings.

BRIEF DESCRIPTION OF DRAWINGS

The present invention will now be described, by way of example with reference to the accompanying drawings, in which:

FIG. 1 is a diagram of a passive entry passive start (PEPS) vehicle security system in accordance with one embodiment.

DETAILED DESCRIPTION

FIG. 1 illustrates a non-limiting example of a passive entry passive start (PEPS) vehicle security system, hereafter the system 10, for a vehicle 12. In general, the system 10 is configured to activate a vehicle function when an activation signal 20 is received from a nomadic device 16. By way of example and not limitation, a vehicle function may include activating a controller 14 that is part of the system 10 to transmit an interrogation signal 28 as part of a communication protocol with the nomadic device 16 to authenticate the nomadic device 16. Authentication is typically determined prior to, for example, unlocking the doors of the vehicle 12, starting the engine of the vehicle 12, or to activating various lights on the vehicle such as interior cabin lights, or exterior lights to illuminate an area about the vehicle 12 and thereby aid an operator 18 approaching the vehicle 12.

The nomadic device 16 is illustrated in this non-limiting example as a key fob 22. Alternatively, the nomadic device 16 could be a smart phone, tablet, or other such portable personal communication device. In general, the nomadic device 16 is configured to detect a change of a magnetic field 30 relative to the nomadic device 16. In this example, the magnetic field 30 is the naturally occurring magnetic field of the Earth as suggested by the North and South designations illustrated. Accordingly, the nomadic device 16 is equipped with a magnetic-field sensor 24, preferable a three-dimensional (3D) magnetic field sensor. A suitable 3D magnetic field sensor is available from AMS-USA Inc., of Raleigh, N.C., USA.

In order to overcome the battery life problems described above, the nomadic device 16 is generally configured to emit an activation signal 20 only if the change of the magnetic field 30 corresponds to walking by an operator 18 carrying the nomadic device 16. It should be understood that an actual change of the magnetic field 30 is not being detected, but an apparent change because the orientation of the nomadic device 16 relative to the magnetic field 30 is being changed by the walking motion of the operator 18. It is emphasized that detecting walking motion is different from detecting if the nomadic device 16 is merely moving toward or away from the vehicle 12. For example, if the nomadic device 16 were being moved closer to the vehicle 12 in a smooth manner such as in a wheel-chair, the nomadic device 16 would not experience any motion comparable to a walking motion, and so the nomadic device 16 would likely not emit the activation signal 20. It should also be appreciated that the controller 14 will not be able to detect the activation signal until the nomadic device 16 is brought within a communication range 26 of the system 10.

The nomadic device 16 may include a processor (not shown) such as a microprocessor or other control circuitry as should be evident to those in the art. The nomadic device 16 may include memory (not shown), including non-volatile memory, such as electrically erasable programmable read-only memory (EEPROM) for storing one or more routines, thresholds and captured data. The one or more routines may be executed by the processor to perform steps for determining if signals output by the magnetic-field sensor 24 indicate a change in the apparent direction of the magnetic field 30 that corresponds to walking or walking motion by the operator 18 carrying the nomadic device 16.

By way of further non-limiting examples, how the processor (not shown) in the nomadic device 16 determines if a signal from the magnetic-field sensor 24 indicates a change that corresponds to walking by an operator 18 carrying the nomadic device 16 are now described. A 3D magnetic-field sensor generally has sensors that indicate magnetic field strength in three axis, for example magnetic field strength for the X-axis, Y-axis, and Z-axis. Using well known geometric formulas, these orthogonal field strengths can be processed to indicate the magnetic field in polar coordinates, and normalized so that apparent changes in the direction of the magnetic field 30 detected by the magnetic-field sensor 24 can be conveyed as an angular change.

When the operator 18 walks while carrying the nomadic device 16, the rhythmic motion associated with walking will cause the direction of the magnetic field detected by the magnetic field sensor to alternate at some frequency indicative of the step cadence of the occupant. Also, the magnitude of the change in angle can be examined to see if it corresponds to a person walking.

In one embodiment, if an angular change greater than a minimum angular threshold, five degrees (5°) for example, and the angular change alternates at a change frequency greater than a minimum frequency threshold, one-tenth of a Hertz (0.1 Hz), then that motion is determined to correspond to walking. It may be preferable to also set upper limits on the angular change and change frequency to avoid unwarranted transmissions of the activation signal 20. As such, the change may also be deemed to correspond to walking by an operator 18 carrying the nomadic device 16 if the angular change is also less than a maximum angular threshold, twenty-five degrees (25°) and/or the change frequency is also less than a maximum frequency threshold, three Hertz (3 Hz), for example.

There may be instances when the operator 18 stops walking to talk to another person or look at something, but it is desirable to have the nomadic device 16 begin transmitting the activation signal as soon as the operator 18 starts walking. In some instances the operator 18 may start walking by turning suddenly, and so a change of the magnetic field relative to the nomadic device that corresponds to an angular change greater than a turning angle threshold, for example ninety degrees (90°) that occurs in less than a turning time threshold, for example one second (1 sec.), may correspond to walking.

It may be advantageous for the nomadic device 16 to be equipped with an indicator 32, such as a light or beeper, which is activated to indicate that the activation signal 20 is being transmitted. Being so equipped will help the operator 18 determine easily that a walking motion has been detected.

Accordingly, a passive entry passive start (PEPS) vehicle security system (the system 10) and a nomadic device 16 is provided. The nomadic device's capability to detect the operator's walking motion improves battery life for the nomadic device and the vehicle with a technique that has minimal nomadic device power overhead. Since the communication time of the system is minimized, security is enhanced by only transmitting signals when the operator is near the vehicle and walking that minimizes the opportunity of relaying or learning the signals by an attacker.

While this invention has been described in terms of the preferred embodiments thereof, it is not intended to be so limited, but rather only to the extent set forth in the claims that follow.

We claim:

1. A passive entry passive start (PEPS) vehicle security system configured to activate a vehicle function when an activation signal is received, said system comprising:
    a nomadic device configured to detect a change of a magnetic field relative to the nomadic device, and emit an activation signal only if the change corresponds to walking by an operator carrying the nomadic device wherein the change corresponds to walking by an operator carrying the nomadic device if an angular change greater than a minimum angular threshold alternates at a change frequency greater than a minimum frequency threshold; wherein the change corresponds to walking by an operator carrying the nomadic device if the angular change is also less than a maximum angular threshold.

2. The system in accordance with claim 1, wherein the change corresponds to walking by an operator carrying the nomadic device if the change frequency is also less than a maximum frequency threshold.

3. The system in accordance with claim 1, wherein the change also corresponds to walking by an operator carrying the nomadic device if the angular change is greater than a turning angle threshold that occurs in less than a turning time threshold.

4. The system in accordance with claim 1, wherein the system is further comprises a controller located in the vehicle, wherein the system is further configured to activate a light on the vehicle if the activation signal is received by the controller.

5. A nomadic device configured to transmit a activation signal to a vehicle equipped with a passive entry passive start (PEPS) vehicle security system configured to activate a vehicle function when an activation signal is received, said nomadic device comprising:
    a magnetic field sensor configured to detect a change of a magnetic field relative to the nomadic device; and
    a processor configured to emit an activation signal only if the change corresponds to walking by an operator carrying the nomadic device wherein the change corresponds to walking by an operator carrying the nomadic device if an angular change greater than a minimum angular threshold alternates at a change frequency greater than a minimum frequency threshold; wherein the change corresponds to walking by an operator carrying the nomadic device if the angular change is also less than a maximum angular threshold.

6. The nomadic device in accordance with claim 5, wherein the change corresponds to walking by an operator carrying the nomadic device if an angular change greater than a minimum angular threshold alternates at a change frequency greater than a minimum frequency threshold.

* * * * *